(12) United States Patent
Tsujita (10) Patent No.: US 11,017,512 B2
(45) Date of Patent: May 25, 2021

(54) BLOOD FLOW IMAGE PROCESSING APPARATUS AND BLOOD FLOW IMAGE PROCESSING METHOD

(71) Applicant: Hitachi, Ltd., Tokyo (JP)

(72) Inventor: Takehiro Tsujita, Tokyo (JP)

(73) Assignee: Hitachi, Ltd., Tokyo (JP)

(*) Notice: Subject to any disclaimer, the term of this patent is extended or adjusted under 35 U.S.C. 154(b) by 15 days.

(21) Appl. No.: 16/361,371

(22) Filed: Mar. 22, 2019

(65) Prior Publication Data
US 2019/0370947 A1 Dec. 5, 2019

(30) Foreign Application Priority Data

May 29, 2018 (JP) .............................. JP2018-102189

(51) Int. Cl.
| | |
|---|---|
| *G06T 5/00* | (2006.01) |
| *G06T 15/50* | (2011.01) |
| *G06T 15/08* | (2011.01) |
| *G06T 5/50* | (2006.01) |
| *A61B 8/06* | (2006.01) |
| *A61B 8/08* | (2006.01) |
| *A61B 8/00* | (2006.01) |
| *A61B 8/14* | (2006.01) |

(52) U.S. Cl.
CPC ................ *G06T 5/009* (2013.01); *A61B 8/06* (2013.01); *A61B 8/466* (2013.01); *A61B 8/488* (2013.01); *A61B 8/5223* (2013.01); *G06T 5/50* (2013.01); *G06T 15/08* (2013.01); *G06T 15/506* (2013.01); *A61B 8/14* (2013.01); *A61B 8/483* (2013.01); *A61B 8/5207* (2013.01); *G06T 2207/10024* (2013.01); *G06T 2207/10072* (2013.01); *G06T 2207/20208* (2013.01); *G06T 2207/20221* (2013.01); *G06T 2207/30104* (2013.01)

(58) Field of Classification Search
None
See application file for complete search history.

(56) References Cited

U.S. PATENT DOCUMENTS

| | | | | |
|---|---|---|---|---|
| 6,480,732 | B1 * | 11/2002 | Tanaka ................. | A61B 8/5238 128/922 |
| 2010/0074493 | A1 * | 3/2010 | Wiemker ................. | A61B 6/12 382/130 |
| 2015/0093005 | A1 * | 4/2015 | Oh ....................... | G01S 7/52068 382/131 |
| 2016/0140738 | A1 * | 5/2016 | Asaka ................. | G01S 15/8995 382/131 |
| 2018/0085088 | A1 * | 3/2018 | Du ...................... | G01S 15/8984 |
| 2019/0269379 | A1 * | 9/2019 | Kapoor ................ | A61B 8/5223 |

FOREIGN PATENT DOCUMENTS

| | | |
|---|---|---|
| JP | 11-206768 A | 8/1999 |
| JP | 3946815 B2 | 7/2007 |
| JP | 4771459 B2 | 9/2011 |

* cited by examiner

*Primary Examiner* — Hilina K Demeter
(74) *Attorney, Agent, or Firm* — Crowell & Moring LLP (57) ABSTRACT

According to one embodiment, a depth map used for a reflection model is generated based on a power image as a blood flow image. A reflection image is generated from the depth map according to the reflection model. By synthesizing the reflection image 70 with the power image, a weighted power image is generated. Using the same method as described above, a weighted velocity image may be generated.

9 Claims, 11 Drawing Sheets

BLOOD FLOW IMAGE PROCESSING APPARATUS AND BLOOD FLOW IMAGE PROCESSING METHOD

BACKGROUND OF THE INVENTION

1. Field of the Invention

The present invention relates to a blood flow image processing apparatus and a blood flow image.

2. Description of Related Art

In the medical field, an ultrasonic diagnostic apparatus is used. The ultrasonic diagnostic apparatus forms an ultrasonic image based on a reception signal obtained by transmission and reception of ultrasonic waves to and from a living organism. As the ultrasonic image, for example, a tomographic image or a blood flow image is known. In general, the blood flow image is a two-dimensional image representing a blood flow in a beam scan surface (two-dimensional data acquisition region) of a living organism.

Specific examples of the blood flow image include a power image and a velocity image. The power image is an image representing a two-dimensional power distribution of Doppler information obtained from a living organism.

The velocity image is an image representing a two-dimensional velocity distribution calculated based on Doppler information obtained from a living organism. In the velocity image, a flow in a positive direction (flow approaching a probe) is represented by, for example, a warm color hue, and a flow in a negative direction (flow moving away from the probe) is represented by, for example, a cold color hue. In this case, the magnitude of velocity in each of the directions is represented by brightness.

Improvement of visibility is desired for a two-dimensional blood flow image. In other words, it is desired to weight a spatial change of a blood flow in a two-dimensional region.

JP-A-H11-206768 describes that a blood flow is represented in a pseudo three-dimensional manner. Japanese Patent No. 3946815 describes that a blood flow velocity distribution is represented in a pseudo three-dimensional manner. However, JP-A-H11-206768 and Japanese Patent No. 3946815 do not describe the generation and use of a pseudo depth map.

SUMMARY OF THE INVENTION

An object of the present invention is to improve the visibility of a blood flow image. Alternatively, an object of the present invention is to weight a spatial change of a blood flow in a two-dimensional region.

According to the present invention, there is provided a blood flow image processing apparatus including: a depth map generating unit for generating a pseudo depth map based on a blood flow image representing a blood flow in a two-dimensional region of a living organism; a weighted image generating unit for generating a weighted image for weighting a spatial change of the blood flow based on the depth map; and a processing unit for processing the blood flow image using the weighted image.

According to the present invention, there is provided a blood flow image processing method that is executed by a blood flow image processing apparatus, the method including: a step of generating a pseudo depth map based on a blood flow image representing a blood flow in a two-dimensional region of a living organism; a step of generating a weighted image for weighting a spatial change of the blood flow from the depth map based on a reflection model; and a step of synthesizing the weighted image with the blood flow image to generate a weighted blood flow image.

The method is implemented by a function of hardware or a function of software. In the latter case, a program for implementing the function is installed on the blood flow image processing apparatus through a portable storage medium or a network. The concept of the blood flow image processing apparatus includes an ultrasonic diagnostic apparatus and an information processing apparatus.

According to the present invention, the visibility of a blood flow image is improved. Alternatively, according to the present invention, a spatial change of a blood flow in a two-dimensional region can be weighted.

DESCRIPTION OF EMBODIMENTS

Hereinafter, an embodiment will be described based on the drawings.

(1) Summary of Embodiment

In a blood flow image processing apparatus according to the embodiment, a depth map generating unit generates a pseudo depth map based on a blood flow image representing a blood flow in a two-dimensional region of a living organism, a weighted image generating unit generates a weighted image for weighting a spatial change of the blood flow based on the depth map, and a processing unit processes the blood flow image using the weighted image.

In order to represent a target three-dimensionally and realistically, various rendering techniques are suggested. Even when any rendering technique is adopted, three-dimensional data of the target is required. The blood flow image is two-dimensional data, and even when a rendering technique is applied to a blood flow image itself, a blood flow cannot be three-dimensionally represented.

On the other hand, according to the above-described configuration, a depth map (elevation map) that is pseudo depth information is artificially generated based on a blood flow image. That is, pseudo three-dimensional data is generated from two-dimensional data. By applying a rendering technique (or three-dimensional representation technique) to a depth map, a weighted image in which a spatial change of a blood flow is weighted is obtained, and a blood flow image is processed based on this weighted image.

In the embodiment, typical examples of the blood flow image include a power image and a velocity image. In the embodiment, a three-dimensional representation model is used for rendering. It is desirable that the three-dimensional representation model is a reflection model. As the reflection model, a specular reflection model and a diffuse reflection model are known. In the embodiment, a specular reflection model is adopted. Other reflection models may be adopted. The concept of processing of a blood flow image includes, for example, synthesis of the weighted image with the blood flow image and correction of the blood flow image based on the weighted image. It is desirable to process the blood flow image such that the magnitude of brightness or a change in hue on the blood flow image is clearly weighted. The blood flow image may be either a moving image or a still image.

In the embodiment, the depth map is generated to apply a reflection model to the blood flow image in a virtual three-dimensional space defined based on the blood flow image, and the weighted image generating unit is a reflection image generating unit for generating a reflection image as the weighted image from the depth map based on the reflection model. The reflection image is an image that exhibits an action of weighting unevenness or magnitude. When the blood flow image is processed based on the reflection image, a spatial change of a blood flow can be weighted.

In the embodiment, the processing unit synthesizes the reflection image with the blood flow image to generate a weighted blood flow image. According to the synthesis of the reflection image, a specific portion in the blood flow image can be weighted. The blood flow image processing apparatus according to the embodiment includes a color converting unit for converting the blood flow image into a color blood flow image, the reflection image is a color image, and the processing unit synthesizes the reflection image as the color image with the color blood flow image. After the synthesis of the two images, color conversion may also be executed. According to the synthesis after the color conversion, the contents of the reflection image can be individually adjusted.

In the embodiment, the reflection image is a white image for displaying gloss. According to this configuration, in the blood flow image, for example, a portion having a high power or a high velocity can be identified, can be three-dimensionally represented, or can be weighted. The white image is an image represented by white or an image represented by a color similar to white or a color that can be identified as white when seen functionally.

In the embodiment, the reflection image generating unit includes a unit for generating a gradient map based on the depth map, and a unit for generating the reflection image based on the gradient map. When the reflection model is applied, the generation of the gradient map is a presupposition. The gradient map is a concept including a normal vector map.

In the embodiment, the blood flow image is a power image representing a power distribution of Doppler information, the depth map generating unit determines each of depths forming the depth map based on each of powers forming the power image, and the depth map generating unit has a function that determines a smaller depth as the power increases. According to this configuration, a portion having a high power in the power image is naturally weighted. For example, this portion is represented to be bright and shiny.

In the embodiment, the blood flow image is a velocity image, the depth map generating unit determines each of depths forming the depth map based on an absolute value of each of velocities forming the velocity image, and the depth map generating unit has a function that determines a smaller depth as the absolute value increases. According to this configuration, a portion having a high absolute value of velocity in the velocity image is naturally weighted. For example, this portion is represented to be bright and shiny.

In the embodiment, the weighted image generating unit generates the weighted image based on the depth map and a dispersion map. Typically, in order to calculate blood flow information, power, velocity, and dispersion are calculated. In the above-described configuration, dispersion is used to generate the weighted image. For example, dispersion may be added to the reflection model instead of roughness of a blood flow surface.

(2) Details of Embodiment

Figure 1:
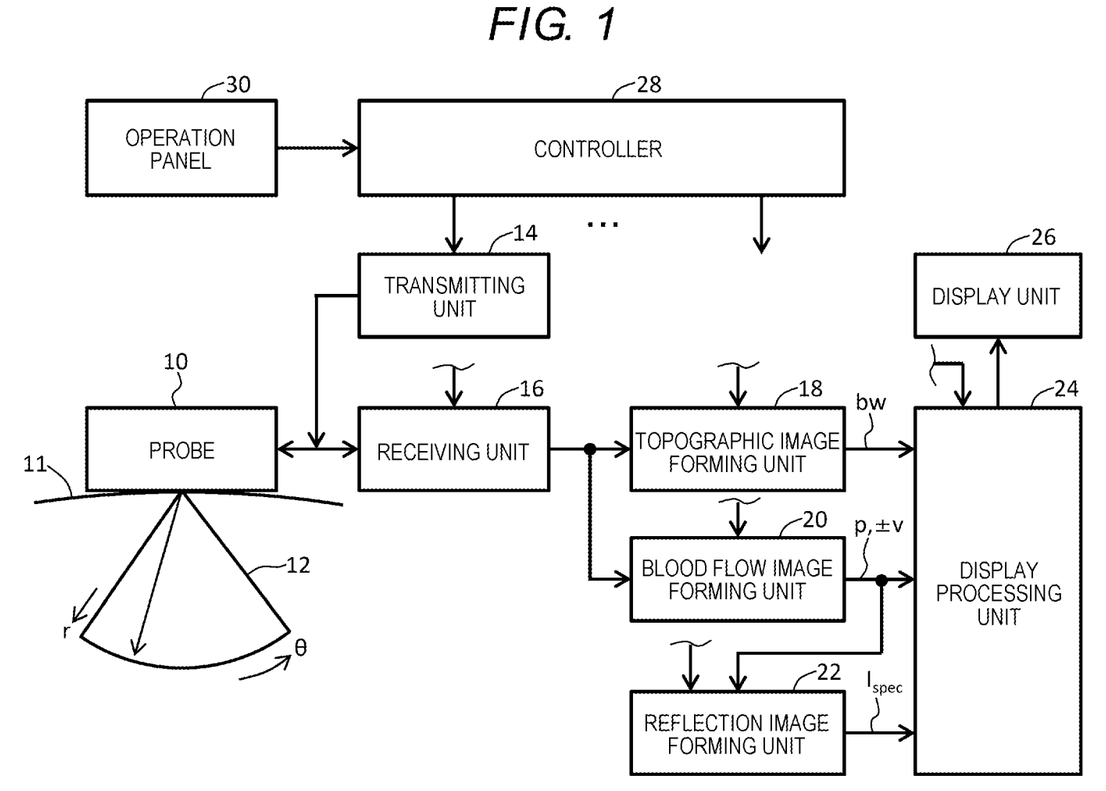
FIG. 1 is a block diagram illustrating a configuration of an ultrasonic diagnostic apparatus according to an embodiment.

FIG. 1 illustrates the blood flow image processing apparatus according to the embodiment. The blood flow image processing apparatus is an ultrasonic diagnostic apparatus that is provided in a medical institution or the like and forms an ultrasonic image based on reception information obtained by transmission and reception of ultrasonic waves to and from a living organism. Examples of the ultrasonic image include a tomographic image representing a biological tissue and a blood flow image representing a blood flow. Examples of the blood flow image include a power image and a velocity image. Blood flow image data generated by an ultrasonic diagnostic apparatus may be processed in an information processing apparatus such as a PC. In this case, the information processing apparatus corresponds to the blood flow image processing apparatus.

In FIG. 1, a probe 10 is a portable transducer. In the example illustrated in the drawing, a transmitting and receiving surface of the probe 10 corresponds to a surface of a living organism 11. The probe 10 includes a vibration element array in which a plurality of vibration elements are arranged in one dimension. An ultrasonic beam is formed by the vibration element array and is electronically scanned. As a result, a beam scan surface 12 is formed. In FIG. 1, a r direction is a depth direction, and an θ direction is an electronic scanning direction. As an electronic scanning method, for example, an electronic sector scanning method and an electronic linear scanning method (including an electronic convex scanning method) are known. A probe that is inserted into a body cavity may be used. Instead of the 1D vibration element array, a 2D vibration element array may be provided. Of course, with the ultrasonic diagnostic apparatus according to the embodiment, a pseudo blood flow image that is three-dimensionally represented can be generated without using a 2D vibration element array. Typically, an ultrasonic beam for forming a tomographic image and an ultrasonic beam for acquiring Doppler information are separately formed.

The transmitting unit 14 is a transmission beam former that outputs a plurality of delayed transmission signals in parallel to the vibration element array during transmission.

A substance of the transmission beam former is an electronic circuit. On the other hand, when reflected waves from a living organism are received by the vibration element array, a plurality of reception signals are output from the vibration element array to the receiving unit 16 in parallel. The receiving unit 16 executes delayed addition (phased addition) on the receiving signals and outputs beam data as the receiving signals having undergone delayed addition. That is, the receiving unit 16 is a reception beam former. A substance of the reception beam former is an electronic circuit. Specifically, the receiving unit 16 includes a plurality of amplifiers, a plurality of A/D converters, a plurality of delay devices, and an adder. In the embodiment, in the receiving unit 16, an orthogonal detection circuit as a complex signal conversion circuit is provided. Reception frame data is composed of a plurality of beam data that are arranged in the electronic scanning direction. Each of the beam data is composed of a plurality of echo data that are arranged in the depth direction.

A tomographic image forming unit 18 functions as a tomographic image forming unit and is an electronic circuit including a beam data processing circuit and a digital scan converter (DSC). The beam data processing circuit is an electronic circuit that applies amplitude calculation, logarithmic conversion, correlation processing, and the like to each of the beam data. The DSC has a coordinate conversion function, an interpolation function, a frame rate conversion function, and the like. A plurality of tomographic image data are generated from a plurality of reception frame data by the DSC. Each of the tomographic image data is B-mode image data representing a section of a biological tissue. Each of the tomographic image data is transmitted to a display processing unit 24. The tomographic image forming unit 18 may be configured by one or more processors that operate according to a program. Alternatively, a controller 28 described below may function as the tomographic image forming unit 18. In FIG. 1, bw represents a pixel value (brightness value) of each of pixels forming a tomographic image.

A blood flow image forming unit 20 functions as a blood flow image forming unit and is an electronic circuit including a Doppler information processing circuit and a digital scan converter (DSC). Each of beam data as a complex signal is input to the Doppler information processing circuit, and a power, a velocity (average velocity), and a dispersion (variation in velocity) are calculated for each of two-dimensional coordinates based on the beam data. Specifically, the Doppler information processing circuit includes a wall motion filter, an autocorrelator, a power calculator, a velocity calculator, and a dispersion calculator. As describe above, the DSC has a coordinate conversion function, an interpolation function, a frame rate conversion function, and the like. The blood flow image forming unit 20 may be configured by one or more processors that operate according to a program. Alternatively, the controller 28 described below may function as the blood flow image forming unit 20. In FIG. 1, p represents a power, and ±v represents a positive or negative velocity. In addition, a dispersion $\sigma$ may be output to the display processing unit 24. The power p, the velocity ±v, and the dispersion $\sigma$ are calculated in units of pixels and are output to the display processing unit 24.

A reflection image generating unit 22 functions as a weighted image generating unit or a reflection image generating unit. The reflection image generating unit 22 is an electronic circuit that artificially generates a pseudo depth map from a blood flow image (power image or velocity image) based on a reflection model as a model for rendering and generates a reflection image based on the depth map. In the embodiment, the reflection image is an image for weighting a portion in the blood flow image having a much higher power or velocity than that of the periphery thereof using glossy feeling. In other words, the reflection image is an image for processing the blood flow image. The reflection image generating unit 22 may be configured by one or more processors that operate according to a program. Alternatively, the controller 28 described below may function as the reflection image generating unit 22. In FIG. 1, $I_{spec}$ represents the intensity, that is, brightness of reflected light in units of pixels. The specific configuration and action of the reflection image generating unit 22 will be described below.

In the embodiment, the reflection image is generated based on the blood flow image having undergone coordinate conversion. Therefore, the DSC is not provided in the reflection image generating unit 22. Of course, the reflection image may be generated based on the blood flow image (reception frame data) before coordinate conversion. In this case, the synthesis of the reflection image with the blood flow image may be executed before or after coordinate conversion. Of course, according to the configuration of the embodiment, as described below, the reflection image as a color image is synthesized with the blood flow image as a color image. Therefore, an advantageous effect can be obtained in that the contents of the reflection image can be individually and freely determined.

The display processing unit 24 functions as a synthesizing unit and a color converting unit and has an image synthesis function, a color conversion function, and the like. The display processing unit 24 configures a display image according to an operation mode or a display mode selected by a user. In a CFM (Color Flow Mapping) mode, a color blood flow image (power image or velocity image) is synthesized with a monochrome B-mode tomographic image to generate a CFM image, and this CFM image is displayed on a display unit 26. When the CFM mode is selected and the user gives an instruction to weight the blood flow image, a color reflection image is synthesized with a color blood flow image (power image or velocity image) to generate a weighted blood flow image. This weighted blood flow image is synthesized with the tomographic image to generate a CFM image, and the CFM image is displayed on the display unit 26.

When the CFM mode is selected, the weighted blood flow image maybe displayed at all times. The type (power image or velocity image) of the blood flow image is selected by the user. The weighted blood flow image may be displayed alone. An intermediate image such as the depth map or the gradient (normal vector) map be displayed. The reflection image may be used for another purpose without being synthesized with the blood flow image. For example, measurement may be executed based on the reflection image. The display processing unit 24 may be configured by one or more processors that operate according to a program. Alternatively, the controller 28 described below may function as the display processing unit 24. The display unit 26 may be configured by a LCD, an organic EL display device, or other display devices.

The controller 28 functions as a control unit and is configured by a CPU and an operation program. The controller 28 controls an operation of each of the configurations illustrated in FIG. 1. In particular, in the embodiment, the controller 28 controls the generation and synthesis of the reflection image. An operation panel 30 is connected to the controller 28. The operation panel 30 is an input device including a plurality of switches, a plurality of buttons, a track ball, and a keyboard. For the definition of the reflection model, various parameters such as a position of a light source or a position of a line of sight (viewpoint) maybe set or changed by the user using the operation panel.

Figure 2:
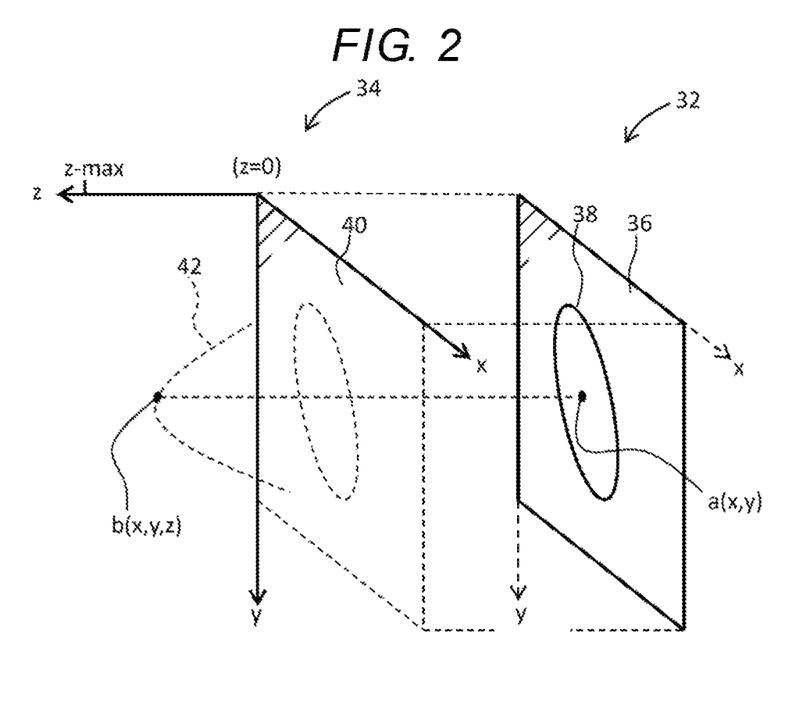
FIG. 2 is a conceptual diagram illustrating a depth map.

FIG. 2 illustrates a method of generating the depth map. A two-dimensional space 32 is defined by an x-axis (horizontal axis) and a y-axis (vertical axis), and a blood flow image 36 is present in the two-dimensional space 32. In a blood flow portion 38, coordinates (x, y) of a point are displayed. On the other hand, a three-dimensional space 34 corresponds to a space in which a z-axis as a depth axis is added to the two-dimensional space 32, and coordinates (x, y, z) of a point b are displayed in the three-dimensional space 34.

In the embodiment, a depth z is calculated for each of pixels forming the blood flow image. Specifically, as described below in detail, the depth z is calculated from a brightness value I (an absolute value of the power p or the velocity V) of a pixel. For this calculation, for example, a conversion formula having an action of decreasing the depth z as the brightness value I increases is used. The three-dimensional space 34 including the depth axis is not a real space and is a virtual space that is artificially defined to apply the reflection model. The x-axis and the y-axis are shared between the two-dimensional space 32 and the three-dimensional space 34. It can also be said that the three-dimensional space 34 is a device defined based on the blood flow image 36. In the three-dimensional space 34, a plurality of depths z are distributed and configure a depth map 42. The minimum value of the depth z is 0, and the maximum value thereof is z-max. For example, z-max is 255. The depth map 42 has a three-dimensional form in the three-dimensional space 34. In the embodiment, the depth map 42 can be considered as a three-dimensional object, and the reflection model is applied thereto.

Figure 3:
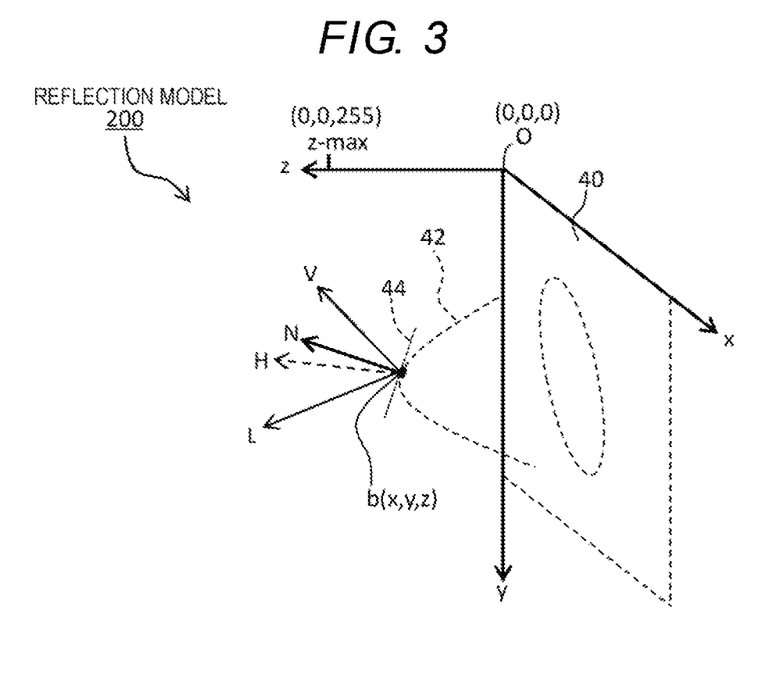
FIG. 3 is a conceptual diagram illustrating a reflection model.

A reflection model (specular reflection model) 200 will be described based on FIG. 3. By considering the depth map 42 as a three-dimensional object, a plane 44 in contact with the point b on the depth map 42 can be defined. The plane 44 has a slope. In the embodiment, the slope is represented by a normal vector N. In addition, regarding the point b, alight vector L and a viewing vector V are defined. A light source and a viewpoint may be determined as fixed points or may be changed by the user. A half vector H is a vector that bisects an angle between the light vector L and the viewing vector V. By applying these vectors to the reflection model, an intensity $I_{spec}$ of reflected light can be calculated regarding the point b. The reflection image is formed as an aggregate of intensities $I_{spec}$ of reflected light calculated for the pixels forming the blood flow image. Regarding rendering for three-dimensionally and realistically a three-dimensional object, various models are suggested. Among the models, it is desirable to adopt a model that can weight a spatial change of a blood flow. In particular, it is desirable to adopt the specular reflection model as described above. A specific calculation formula will be described below.

Figure 4:
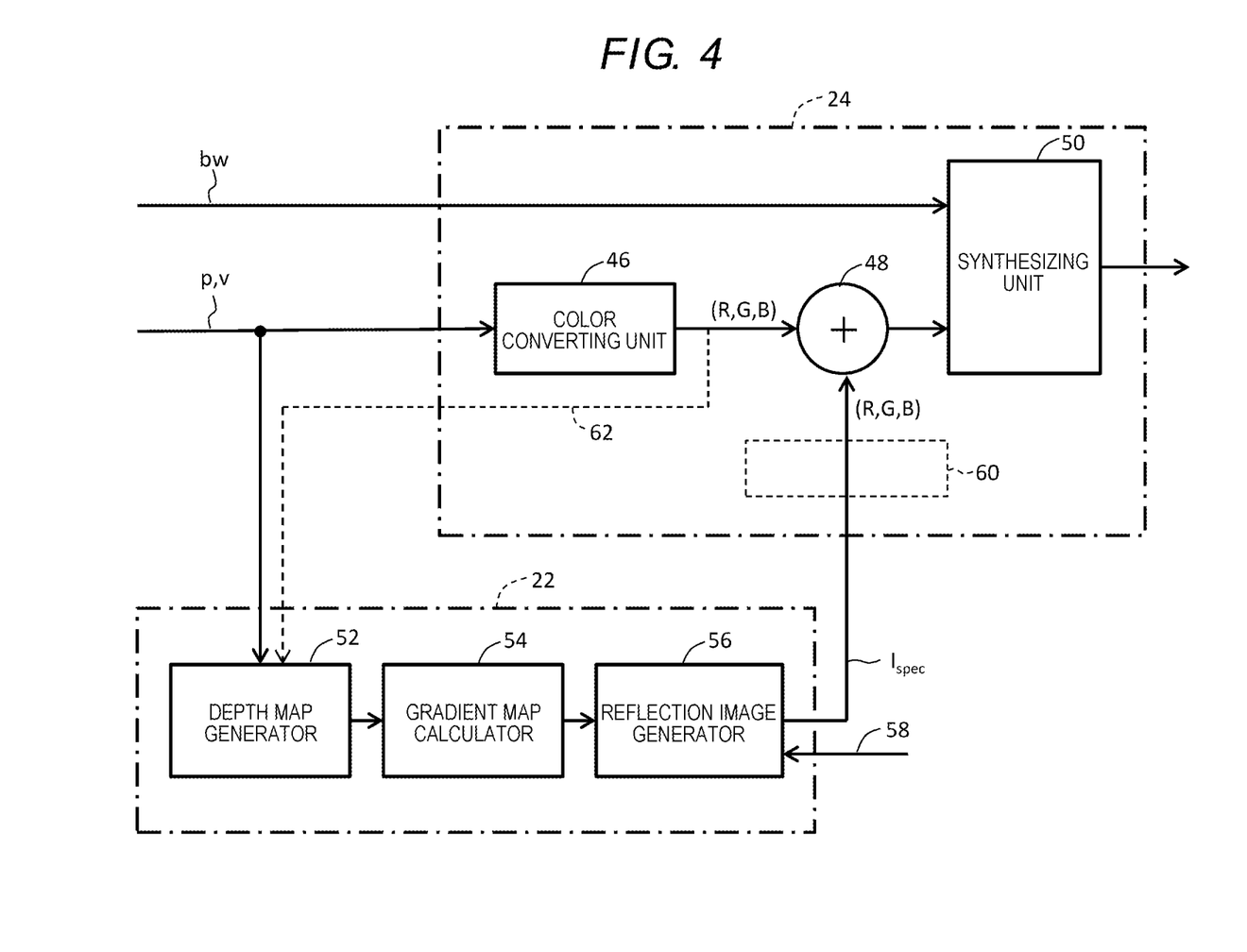
FIG. 4 is a block diagram illustrating a first configuration example of a reflection image generating unit and a display processing unit.

FIG. 4 illustrates a first configuration example of the reflection image generating unit and the display processing unit; The display processing unit 24 includes: a color converting unit 46 that functions as the color converting unit; an adder 48 that functions as the processing unit or the synthesizing unit; and a synthesizing unit 50. The color converting unit 46 converts the blood flow image (power image or velocity image) into a color image. The adder 48 synthesizes the weighted image as a color image with the blood flow image as a color image to generate a weighted blood flow image. The synthesizing unit 50 synthesizes the weighted blood flow image as a color image and a monochrome tomographic image as a background image with each other.

The reflection image generating unit 22 includes a depth map generator 52, a gradient map calculator 54, and a reflection image generator 56. The depth map generator 52 functions as the depth map generating unit, and the power image or the velocity image is input thereto as the blood flow image. When the power image is input to the depth map generator 52, the depth map generator 52 converts a power into a depth for each of pixels in the power image. As a result, a depth map composed of a plurality of depths is generated. When the velocity image is input to the depth map generator 52, the depth map generator 52 converts an absolute value of velocity into a depth for each of pixels in the velocity image. As a result, a depth map composed of a plurality of depths is generated. Any one of the depth maps does not represent an actual depth distribution and is pseudo morphological information that is artificially generated to apply the reflection model.

In the depth map generator 52, when the depth z is obtained from the power p, for example, the following Formula (1) is calculated.

[Formula 1]

$$z=k*(255-p) \quad (1)$$

In Formula (1), the minimum value of the depth z is 0, and the maximum value of the depth z is 255. The power p is subtracted from 255 as the maximum value to obtain a value, and the obtained value is multiplied by a coefficient k. As a result, the depth z is calculated. According to Formula (1), as the power p increases, a smaller depth z is calculated.

On the other hand, in the depth map generator 52, when the depth z is obtained from the velocity v, for example, the following Formula (2) is calculated.

[Formula 2]

$$z=k*(255-|v|*2) \quad (2)$$

In Formula (2), likewise, the minimum value of the depth z is 0, and the maximum value of the depth z is 255. The absolute value of the velocity v is subtracted from 255 as the maximum value to obtain a value, and the obtained value is doubled and multiplied by the coefficient k. As a result, the depth z is calculated. According to Formula (2), as the absolute value of the velocity v increases, a smaller depth z is calculated.

By using a lookup table (LUT) instead of the formula calculation, the depth z may be calculated from the power p or the velocity v. For example, the following Formula (3-1) or (3-2) may be used. In these formulae, lut represents conversion in LUT.

[Formula 3]

$$z=k*lut(p) \quad (3\text{-}1)$$

$$z=k*lut(|v|) \quad (3\text{-}2)$$

As shown in the following Formula (4), the depth z may be calculated based on a desired function f(I) such as a polynomial or a logarithm function. Here, I as an argument of the function represents brightness, and the brightness I represents the power p or the absolute value of the velocity v.

[Formula 4]

$$z=k*f(I) \quad (4)$$

In FIG. 4, the gradient map calculator 54 functions as a gradient map calculating unit and executes spatial differentiation on the depth map to generate a gradient map. Specifically, a slope of a plane in contact with each of points on the depth map is calculated. As a result, a gradient map as a distribution of the slopes is generated. Actually, as the slope of the plane in contact with each of the points, a normal vector of the plane is calculated. That is, in the embodiment, the gradient map is generated as a normal vector map.

The reflection image generator 56 forms a main part of the reflection image generating unit and generates the reflection image based on the gradient map (normal vector map). Specifically, for example, the brightness $I_{spec}$ of each of the pixels forming the reflection image (the intensity of reflected light when observed at the viewpoint) is calculated based on the following Formula (5) according to the reflection model (specular reflection model).

[Formula 5]

$$I_{spec} = \frac{\rho_s \cdot F(H, L) \cdot D \cdot G(H, L, V, N)}{\pi (N \cdot V)(N \cdot L)} \quad (5)$$

In a numerator of Formula (5), $\rho_s$ represents a specular reflection coefficient. F is a Fresnel term and is defined by the half vector H and the light vector L. D represents a distribution function or a normal distribution term and corresponds to a variation of an object surface. G is a geometric attenuation term and is defined by the half vector H, light vector L, the viewing vector V, and the normal vector N. A denominator in Formula (5) includes the inner product of the normal vector N and the viewing vector V and the inner product of the normal vector N and the light vector L. Formula (5) itself is a well-known calculation formula. As represented by reference numeral 58, parameters required to calculate the intensity of the reflected light are given to the user. In this case, preset parameters may also be used. The parameters may be automatically determined based on transmission/reception conditions of ultrasonic waves or Doppler information.

The distribution function D may also be a function of the dispersion σ of the blood flow velocity. In this case, the intensity $I_{spec}$ of reflected light is calculated according to the following Formula (6).

[Formula 6]

$$I_{spec} = \frac{\rho_s \cdot F(H, L) \cdot D(H, N, \sigma) \cdot G(H, L, V, N)}{\pi (N \cdot V)(N \cdot L)} \quad (6)$$

The dispersion σ may be used instead of the distribution function D. The use of the dispersion σ is shown in the following Formula (7).

[Formula 7]

$$I_{spec} = \frac{\rho_s \cdot F(H, L) \cdot \sigma \cdot G(H, L, V, N)}{\pi (N \cdot V)(N \cdot L)} \quad (7)$$

According to Formula (7), the calculation amount can be reduced. Furthermore, a reflection image on which the dispersion σ is further reflected can be obtained. The dispersion σ is calculated for the coordinates (x, y). A dispersion map is generated from a plurality of dispersions σ corresponding to a plurality of pixels.

In FIG. 4, the reflection image generated as described above is superimposed on the blood flow image having undergone color conversion in the adder 48. In the embodiment, the reflection image is configured as a white image, and a ratio between R, G, and B is 1:1:1. When this reflection image is synthesized as the power image, a portion having a high power is weighted to be bright. When this reflection image is synthesized as the velocity image, a portion having a high absolute value of velocity is weighted to be bright.

A color addition unit 60 may be additionally added to color the reflection image in the color converting unit 46. Another processing unit may be provided instead of the adder 48. For example, correction for weighting the hue or brightness of the blood flow image based on the reflection image may be executed. A blood flow image 62 having undergone color conversion is transmitted to the depth map generator 52, and a depth map is generated based on the blood flow image 62. A processing method suitable for the circumstances may be automatically or manually selected from a plurality of processing methods.

Figure 5:
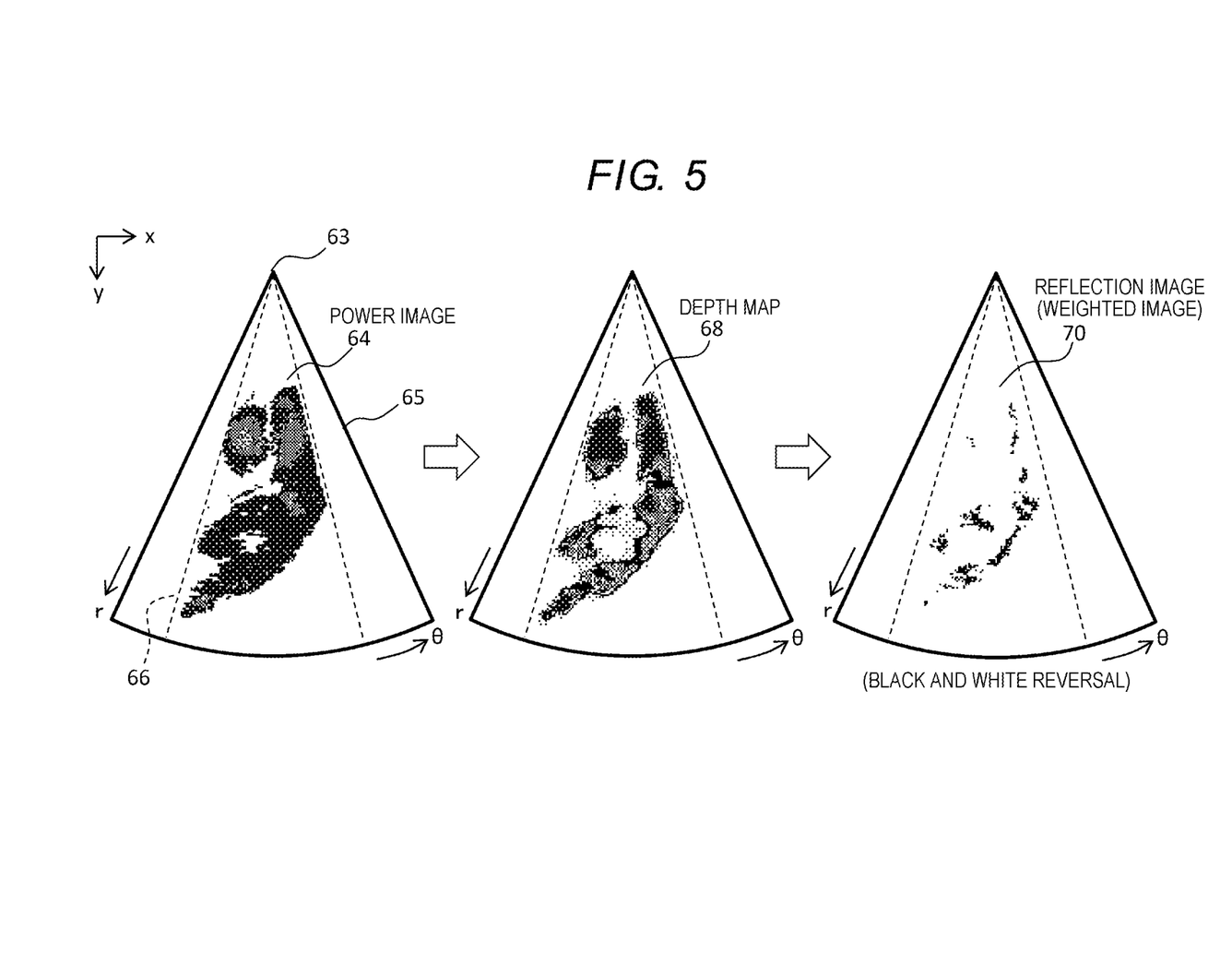
FIG. 5 is a diagram illustrating the generation of a reflection image.

FIG. 5 illustrates the process of generating the reflection image. A region of interest (ROI) 66 is determined in a display area 65, and a power image 64 is present in the region of interest 66. Reference numeral 63 represents a transmission/reception starting point. The region of interest 66 is, for example, a region that covers a part or the entire area of a left ventricle of a heart. In the embodiment, a depth map 68 is generated based on the power image (the power image before color conversion or the power image having undergone color conversion). The depth map corresponds to a power distribution in a two-dimensional area. Under the reflection model, a reflection image 70 is generated based on the depth map 68. The reflection image 70 is a weighted image for weighting a spatial change of a blood flow. In the embodiment, the reflection image is a white image. However, FIG. 5 illustrates a reflection image having undergone black and white reversal for convenience of observation.

Figure 6:
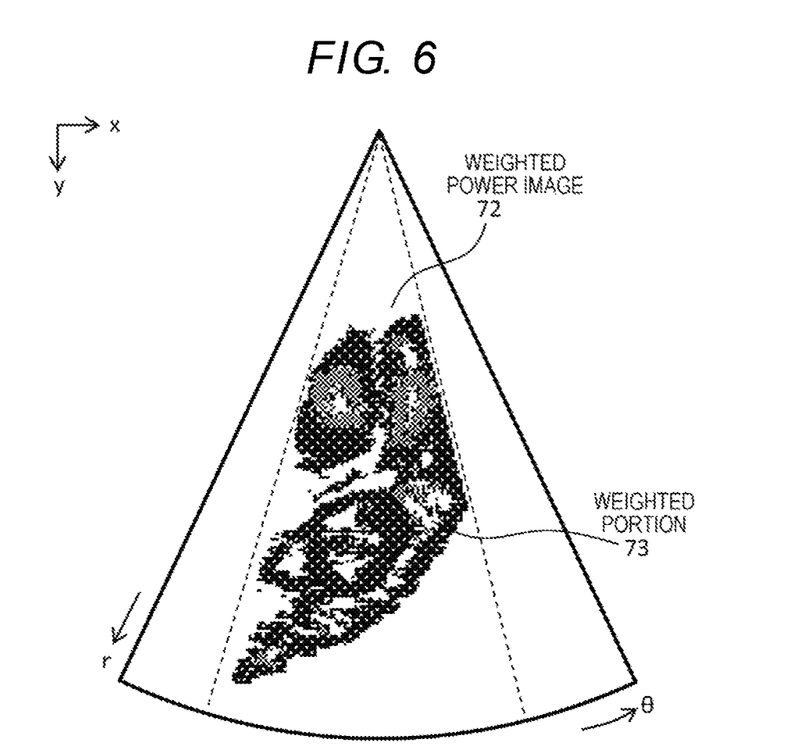
FIG. 6 is a diagram illustrating an example of a weighted power image.

FIG. 6 illustrates a weighted power image 72. This weighted power image 72 is generated by synthesizing the reflection image with the power image illustrated in FIG. 5. A portion having a higher power is a weighted portion 73. That is, this portion is represented by white or gloss. As a result, a spatial change of a blood flow can be clearly represented, and the visibility of the power image can be improved.

Figure 7:
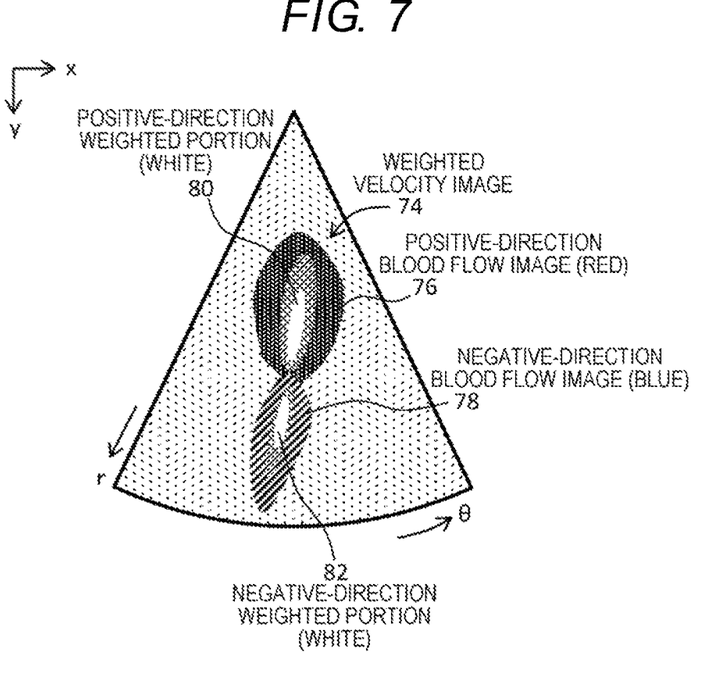
FIG. 7 is a diagram illustrating an example of a weighted velocity image.

FIG. 7 illustrates a weighted velocity image 74. This weighted velocity image 74 is generated by synthesizing the reflection image with the velocity image. A portion having a high absolute value of velocity is weighted. Specifically, a positive-direction blood flow image 76 represented by a warm color includes a positive-direction weighted portion 80, and a negative-direction blood flow image 78 represented by a cold color includes a negative-direction weighted portion 82. These weighted portions 80 and 82 are represented by white or represented to be bright. As a result, a spatial change of a blood flow can be clearly represented, and the visibility of the velocity image can be improved. In particular, the visibility of regurgitation caused by valvular insufficiency can be improved.

Figure 8:
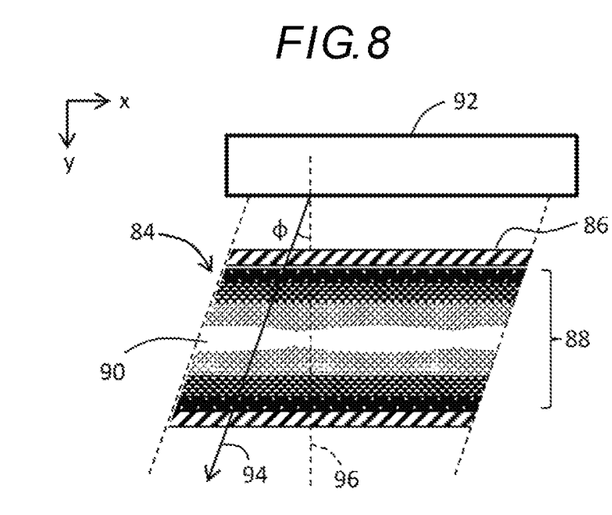
FIG. 8 is a diagram illustrating another weighted blood flow image.

FIG. 8 illustrates a carotid artery. A power image 84 is represented in an inner portion 88 of a vascular wall 86. A central portion 90 having a high power is weighted by being synthesized with the reflection image. An ultrasonic beam 94 that is inclined from a vertical axis perpendicular to a probe 92 by a deflection angle φ is linearly scanned. As a result, the power image 84 is formed.

Figure 9:
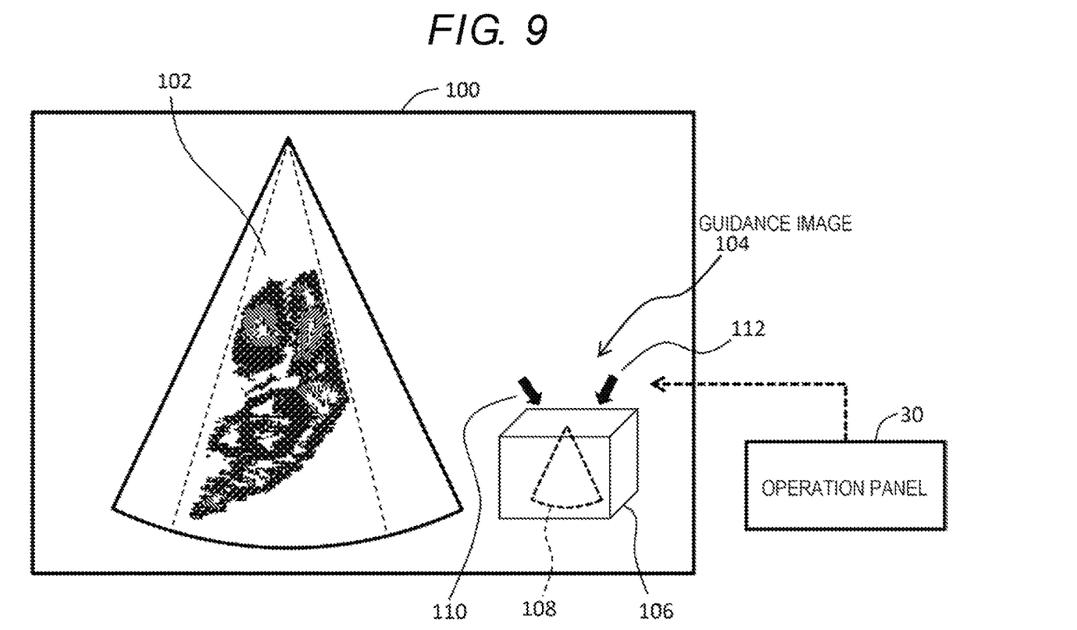
FIG. 9 is a diagram illustrating an operation of a guidance image.

FIG. 9 illustrates another display example. A guidance image 104 adjacent to a weighted blood flow image 102 may be displayed. The guidance image 104 includes, for example, a wire frame 106 representing a three-dimensional space, a mark 108 representing a beam scan surface, a mark 110 representing a light source, and a mark 112 representing a viewpoint. For example, the positions of the light source and the viewpoint may be changed by operating the marks 110 and 112 using the operation panel 30. In this case, an optimum combination of the position of the light source and the position of the viewpoint may be found while observing the reflection image that changes in real time. Projection light parallel to the z direction and a line of sight parallel to the z direction may be set.

Figure 10:
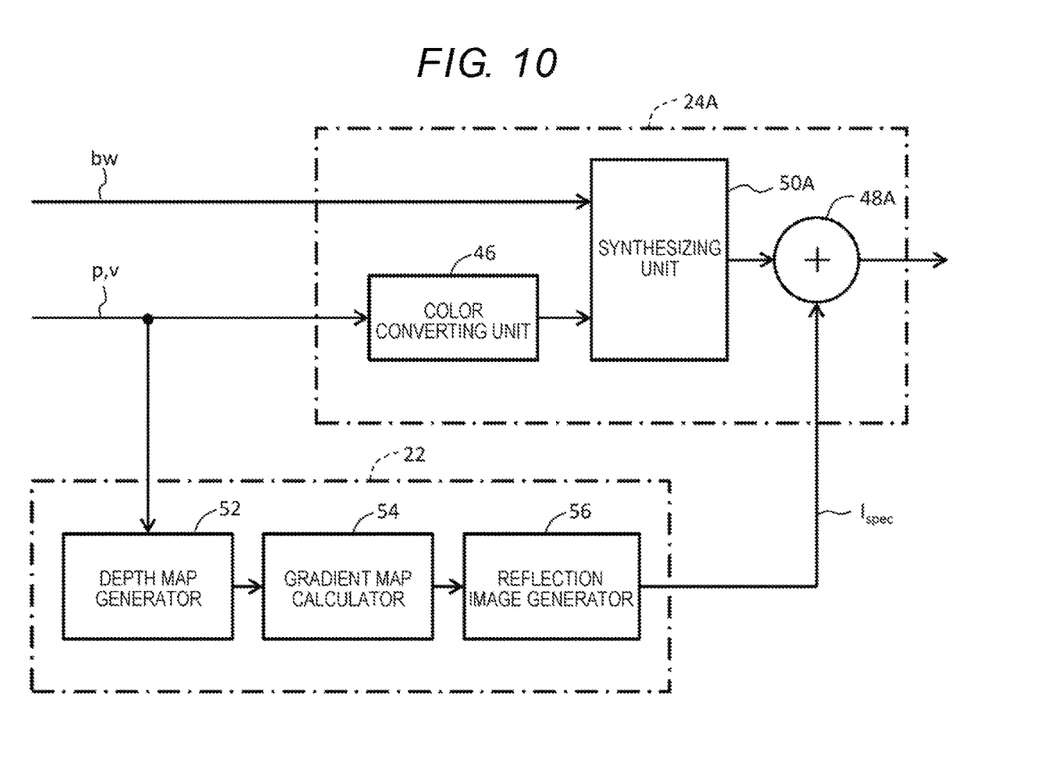
FIG. 10 is a block diagram illustrating a second configuration example of the reflection image generating unit and the display processing unit.

FIG. 10 illustrates a second configuration example of the reflection image generating unit and the display processing unit; In FIG. 10, the same configurations as those of FIG. 4 are represented by the same reference numerals, and the description thereof will not be repeated. In the second configuration example, in a display processing unit 24A, a synthesizing unit 50A is provided at a previous stage of a multiplier 48A. That is, the blood flow image and the tomographic image are synthesized with each other, and then the reflection image is synthesized with the synthetic image. Even with this configuration, the blood flow image can be weighted. When the tomographic image is synthesized after synthesizing the blood flow image and the reflection image, the reflection image may overlap the tomographic image. However, according to the second configuration example, this problem can be avoided.

Figure 11:
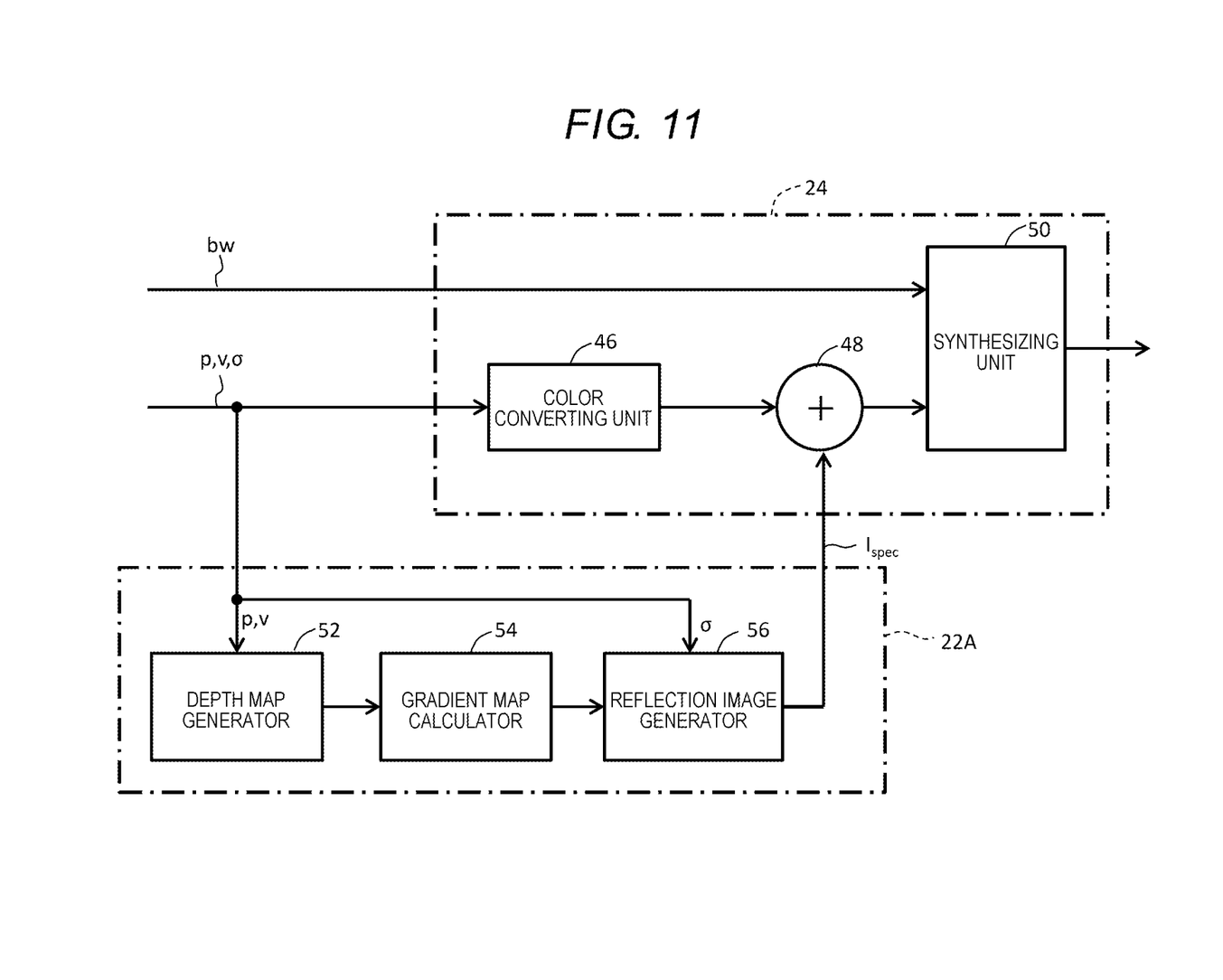
FIG. 11 is a block diagram illustrating a third configuration example of the reflection image generating unit and the display processing unit.

FIG. 11 illustrates a third configuration example of the reflection image generating unit and the display processing unit; In FIG. 11, the same configurations as those of FIG. 4 are represented by the same reference numerals, and the description thereof will not be repeated. In the third configuration example, the dispersion σ is input to the reflection image generator 56 in a reflection image generating unit 22A, and the reflection image is generated in consideration of the dispersion σ. In this case, for example, Formula (6) or (7) is used. According to the third configuration example, the dispersion can be reflected on the reflection image. Therefore, that is, the variation in velocity can be represented on the reflection image.

Figure 12:
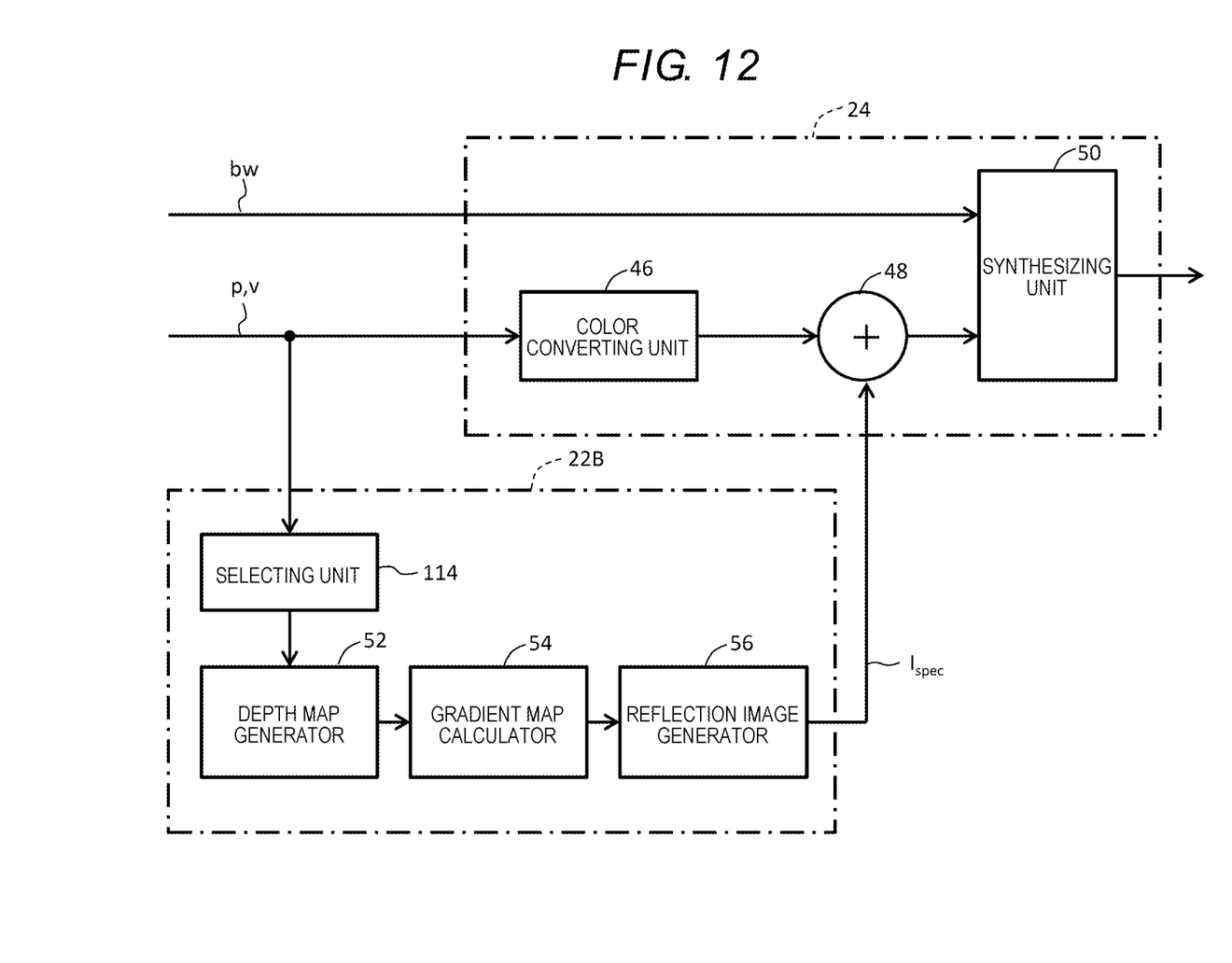
FIG. 12 is a block diagram illustrating a fourth configuration example of the reflection image generating unit and the display processing unit.

FIG. 12 illustrates a fourth configuration example of the reflection image generating unit and the display processing unit; In FIG. 12, the same configurations as those of FIG. 4 are represented by the same reference numerals, and the description thereof will not be repeated. In the fourth configuration example, in a reflection image generating unit 22B, a selecting unit 114 is provided at a previous stage of the depth map generator. The selecting unit 114 has a function of selecting any one of the power image and the velocity image and has a function of selecting either or both of a component in the positive direction and a component in the negative direction when the velocity image is selected. For example, when the component in the negative direction is selected by the selecting unit, the reflection image is generated based on the component in the negative direction. In the blood flow image, the flow in the negative direction, for example, regurgitation can be weighted. Only the flow in the positive direction may be weighted. Alternatively, the flow in the positive direction and the flow in the negative direction may be separately weighted.

According to the embodiment, a depth map (elevation map) that is pseudo depth information is artificially generated based on a blood flow image. That is, pseudo three-dimensional data is generated from two-dimensional data. By applying a rendering technique (or three-dimensional representation technique) to a depth map, a weighted image in which a spatial change of a blood flow is weighted is obtained, and a blood flow image is weighted based on this weighted image. In the embodiment, the reflection image is synthesized with the blood flow image. However, a modification example in which the reflection image is synthesized with another image can be considered. For example, the reflection image may be synthesized with a B-mode image. The reflection image alone may be a target to be measured. A plurality of reflection images having different representation methods may be generated to be weighted and synthesized with the blood flow image. The above-described processing may be applied to surface data (a two-dimensional blood flow image) cut out from volume data.

What is claimed is:

1. A blood flow image processing apparatus comprising:
a depth map processor that generates a pseudo depth map based on a two-dimensional blood flow image representing a blood flow in a two-dimensional region of a living organism, the pseudo depth map being formed from multiple pseudo depths that are created from multiple brightness values that form the two-dimensional blood flow image;
a weighted image processor that generates a weighted image for weighting a spatial change of the blood flow based on the depth map; and
an image processor that processes the blood flow image using the weighted image; wherein
the blood flow image is a power image representing a power distribution of Doppler information;
the depth map processor determines each of depths forming the depth map based on each of powers forming the power image; and
the depth map processor has a function that determines a smaller depth as the power increases.

2. The apparatus according to claim 1, wherein
the depth map is generated to apply a reflection model to the blood flow image in a virtual three-dimensional space defined based on the blood flow image, and
a reflection image processor is configured as the weighted image processor, and wherein said reflection image processor generates a reflection image as the weighted image from the depth map based on the reflection model.

3. The apparatus according to claim 2, wherein
the image processor synthesizes the reflection image with the blood flow image to generate a weighted blood flow image.

4. The apparatus according to claim 3, further comprising a color conversion processor that converts the blood flow image into a color blood flow image, wherein
the reflection image is a color image, and
the image processor synthesizes the reflection image as the color image with the color blood flow image.

5. The apparatus according to claim 4, wherein
the reflection image is a white image for displaying gloss.

6. The apparatus according to claim 2, wherein
the reflection image processor includes:
a gradient map processor that generates a gradient map based on the depth map; and
a reflection generation processor that generates the reflection image based on the gradient map.

7. The apparatus according to claim 1, wherein
the weighted image processor generates the weighted image based on the depth map and a dispersion map.

8. A blood flow image processing method that is executed by a blood flow image processing apparatus, the method comprising steps of:
generating a pseudo depth map based on a two-dimensional blood flow image representing a blood flow in a two-dimensional region of a living organism, the pseudo depth map being formed from multiple pseudo depths that are created from multiple brightness values that form the two-dimensional blood flow image;
generating a weighted image for weighting a spatial change of the blood flow from the depth map based on a reflection model; and
synthesizing the weighted image with the blood flow image to generate a weighted blood flow image; wherein
the blood flow image is a power image representing a power distribution of Doppler information;
the depth map processor determines each of depths forming the depth map based on each of powers forming the power image; and
the depth map processor has a function that determines a smaller depth as the power increases.

9. A non-transitory computer-readable storage medium storing a blood-flow imaging program that, when executed, causes a processor to:
generate a pseudo depth map based on a two-dimensional blood flow image representing a blood flow in a two-dimensional region of a living organism, the pseudo depth map being formed from multiple pseudo depths that are created from multiple brightness values that form the two-dimensional blood flow image;
generate a weighted image for weighting a spatial change of the blood flow from the depth map based on a reflection model; and
synthesize the weighted image with the blood flow image to generate a weighted blood flow image; wherein
the blood flow image is a power image representing a power distribution of Doppler information;
the depth map processor determines each of depths forming the depth map based on each of powers forming the power image; and
the depth map processor has a function that determines a smaller depth as the power increases.

* * * * *